United States Patent [19]

Ogawa et al.

[11] Patent Number: 5,139,760
[45] Date of Patent: Aug. 18, 1992

[54] AMORPHOUS SILICA-ALUMINA SPHERICAL PARTICLES AND PROCESS FOR PREPARATION THEREOF

[75] Inventors: Masahide Ogawa; Kiyoshi Abe; Kazuhiko Suzuki, all of Shibata; Hiroshi Ogawa, Nakajo, all of Japan

[73] Assignee: Mizusawa Industrial Chemicals, Ltd., Tokyo, Japan

[21] Appl. No.: 484,869

[22] Filed: Feb. 26, 1990

[30] Foreign Application Priority Data

Feb. 28, 1989 [JP] Japan ................................. 1-45330

[51] Int. Cl.$^5$ ............................................. C01B 33/26
[52] U.S. Cl. .................................. 423/328; 502/263; 585/17; 428/402
[58] Field of Search ................... 423/328, 329, 330; 502/239, 242, 263; 585/17; 428/315

[56] References Cited

U.S. PATENT DOCUMENTS

| 2,786,758 | 3/1957 | Taylor | 423/328 |
|---|---|---|---|
| 2,990,247 | 6/1961 | Conrad et al. | 423/328 |
| 3,784,392 | 1/1974 | Bertorelli | 423/328 |
| 4,268,574 | 5/1981 | Peccenini et al. | 423/328 |
| 4,959,268 | 9/1990 | Hagiwara et al. | 423/328 |

FOREIGN PATENT DOCUMENTS

| 1542644 | 5/1970 | Fed. Rep. of Germany | 423/328 |
|---|---|---|---|
| 53-26793 | 3/1978 | Japan | 423/328 |
| 62-70220 | 3/1987 | Japan | 423/328 |
| 1-257124 | 10/1989 | Japan | 423/328 |

Primary Examiner—R. Bruce Breneman
Attorney, Agent, or Firm—H. Jay Spiegel

[57] ABSTRACT

Disclosed are amorphous silica-alumina spherical particles having a notched surface. The particles have a small specific surface area and a highly controlled hygroscopic property. The spherical particles are obtained by exchanging at least a part of an alkali metal ion of a P-type zeolite as the starting material with a divalent metal and firing the ion-exchanged zeolite. Since the pH value is shifted to a weakly alkaline level by the ion exchange treatment, the particles are effective as a filler for stabilizing a resin or the like when incorporated therein, and the refractive index of the particles can be made close to that of a resin in which the particles are to be incorporated.

7 Claims, 3 Drawing Sheets

AMORPHOUS SILICA-ALUMINA SPHERICAL PARTICLES AND PROCESS FOR PREPARATION THEREOF

BACKGROUND OF THE INVENTION

(1) Field of the Invention

The present invention relates to amorphous silica-alumina spherical particles having a novel particulate form and characteristics desirable for a filler or pigment, and a process for the preparation thereof.

(2) Description of the Prior Art

Amorphous silica or alumina spherical particles are widely used as a filler for various polymer films and other resins and rubbers, a filler for cosmetics, a supporting carrier for perfumes and chemicals, a filler for the chromatography, and the like.

As the means for producing such silica-alumina spherical particles, processes are known in which a silica-alumina is sprayed and, according to need, the sprayed sol is caused to impinge against an air current, a process in which an organic metal compound is hydrolyzed, and a process in which a crystalline zeolite having a cubic or spherical particulate form is neutralized under such conditions that the crystal structure is substantially destroyed but the particulate form is not substantially destroyed, to remove the alkali metal component from the zeolite.

The silica-alumina spherical particles prepared according to the former process are disadvantageous in that the primary particle size is relatively coarse and the particle size distribution is broad.

For example, when these spherical particles are used as a filler for a resin, a problem arises with respect to the dispersibility in the resin or the compatibility therewith. Namely, if the resin having these silica-alumina spherical particles incorporated therein is formed into a film and the film is drawn, voids (vacant spaces) are readily formed between the resin and the filler particles.

The last-mentioned process is very valuable as the process for the production of amorphous silica particles, but since the alumina component in the zeolite is considerably removed together with the soda component during acid treatment, the alumina component is lost and the particles are structurally changed, and the refractive index of the particles is drastically changed. Therefore, the process is not desirable as the process for the preparation of amorphous silica-alumina particles.

The fatal defect of the conventional silica-alumina spherical particles is that the spherical particles still retain the characteristics of the amorphous silica-alumina adsorbent. Accordingly, if the known silica-alumina spherical particles are incorporated into a resin, blowing is caused when the resulting composition is heat-shaped.

SUMMARY OF THE INVENTION

We found that if a P-type zeolite described hereinafter is ion-exchanged with a specific divalent metal, such as an element of group II of the Periodic Table, and is then fired, the ion-exchanged zeolite is readily rendered amorphous, the strongly alkaline particles are converted to weakly alkaline particles by the ion exchange treatment and the hygroscopic characteristics of the zeolite are drastically reduced while the particles are rendered amorphous by the firing, and that by appropriately selecting the divalent metal seed, a refractive index can be adjusted to a level suitable for incorporation into a resin or the like. We have now completed the present invention based on these findings.

Namely, it is a primary object of the present invention to provide amorphous silica-alumina spherical particles having a definite spherical particulate form, a reduced hygroscopic property, a high refractive index and, desirably a sharp particle size distribution and a high whiteness, and a process for the preparation thereof.

Another object of the present invention is to provide amorphous silica-alumina spherical particles having a novel particulate form and characteristics of a filler or a pigment, and a process for the preparation thereof.

More specifically, in accordance with one aspect of the present invention, there is provided a process for the preparation of silica-alumina spherical particles, which comprises the step of synthesizing zeolite particles having an X-ray diffraction pattern peculiar to the P-type zeolite, each zeolite particle having a definite spherical form as a whole and a notched surface, the step of exchanging at least a part of an alkali metal ion in the zeolite particles with a divalent metal ion, especially a Ca, Mg, Zn, Ba or Sr at a temperature of 200° to 700° C.

In accordance with another aspect of the present invention, there is provided amorphous silica-alumina spherical particles having a chemical composition represented by the following formula:

$$mMO \cdot nNa_2O \cdot pSiO_2 \cdot Al_2O_3 \cdot qH_2O$$

wherein M represents at least one member selected from the group consisting of divalent metals, especially Ca, Mg, Zn, Ba and Sr, $m+n$ is a number of $1.1\pm 0.2$, the m/n ratio is in the range of from 10/0 to 1/9, p is a number of $4\pm 1.5$ and q is a number smaller than 0.5, each particle having a definite spherical form as a whole and a notched surface, wherein the moisture absorption determined after standing at a relative humidity of 90% and room temperature for 48 hours is lower than 13% and the refractive index is 1.48 to 1.61.

The present invention is based on the finding that among various zeolites, the P-type zeolite has such an exceptional property that if the sodium ion is exchanged with a metal ion and the ion-exchanged zeolite is fired, the zeolite is easily rendered amorphous and simultaneously, the hygroscopic property can be controlled to a very low level.

Since the starting P-type zeolite has a sodium component in the molecule structure, a 5% aqueous dispersion of this zeolite has such a high pH value as almost 11 and the zeolite has a high alkalinity. According to the present invention, by the ion exchange of the sodium component with a divalent metal ion, a similar aqueous dispersion has a pH value of 7 through 9, and it is obvious that the zeolite is modified to a weakly alkaline product by this ion exchange. Accordingly, when the amorphous silica-alumina particles of the present invention are incorporated into a resin or the like, the deterioration of the resin or the like is prominently controlled and the stability of the resulting resin composition is conspicuously improved. This tendency is especially advantageous when the particles are incorporated as a filler in an easily hydrolyzable resin such as a polyester or a polyamide or as a paper filler, an agricultural chemical carrier, a cosmetic additive or a painting additive.

The second characteristic feature of the amorphous silica-alumina spherical particles of the present invention is that the hygroscopic property is controlled to a level much lower than that of the conventional zeolite or the conventional amorphous silica-alumina filler. The hygroscopic property of the conventional silica-alumina is due to a high surface activity thereof, and the hygroscopic property of the conventional zeolite is due to the presence of fine pores inherently possessed by the tectoaluminosilicate. The reason why the amorphous silica-alumina particles of the present invention have only a low hygroscopic property is considered to be that the destruction of the tectoaluminosilicate is advanced without increase of the surface area by the ion exchange and firing with the blockade of the above-mentioned fine pores.

The third characteristic feature of the amorphous silica-alumina spherical particles is that since the sodium component is ion-exchanged with the divalent metal component, the refractive index is shifted to a higher side, that is, a level of 1.48 to 1.63, especially 1.49 to 1.53. The P-type zeolite used as the starting material of the present invention has a refractive index lower than 1.48, but if this P-type zeolite is ion-exchanged, the refractive index is elevated to a level matched with the refractive index of a resin in which the ion-exchanged zeolite is to be incorporated, while the amorphous state is maintained. Furthermore, according to the present invention, by appropriately selecting the kind of the divalent metal, the refractive index can be easily adjusted to a desirable level.

The amorphous silica-alumina of the present invention is further characterized in that the respective particles have a definite spherical shape as a whole and a notched surface.

DETAILED DESCRIPTION OF THE PREFERRED EMBODIMENTS

Figure 1:
FIG. 1 is an electron microscope photo (10,000 magnifications) of amorphous silica-alumina particles (sample 1-2) of the present invention.

The present invention will now be described in detail.

Starting Material

In the production of amorphous silica-alumina spherical particles of the present invention, zeolite particles having an X-ray diffraction pattern peculiar to the P-type zeolite, each particle having a definite spherical particulate form and a stain-like notched surface, are first prepared.

The P-type zeolite having this particulate form is prepared by mixing sodium silicate, active silicic acid gel or silica sol with metakaolin, sodium aluminate or alumina sol and sodium hydroxide under conditions described below to form an alkali metal alumino-silicate gel, homogenizing the gel and crystallizing the gel at a temperature of 80° to 200° C. under atmospheric pressure or under hydrothermal reaction conditions.

| Component Ratio | Mixing Conditions Molar Ratio | Preferred Molar Ratio |
|---|---|---|
| $Na_2O/SiO_2$ | 0.2 to 8 | 0.5 to 2.0 |
| $SiO_2/Al_2O_3$ | 3 to 20 | 4 to 10 |
| $H_2O/Na_2O$ | 20 to 200 | 30 to 100 |

The formed zeolite is washed with water, and after the classification treatment to a predetermined particle size, the zeolite is subjected to the ion exchange treatment.

An example of the chemical composition of the starting P-type zeolite is represented by the following formula:

$$kNa_2O \cdot pSiO_2 \cdot Al_2O_3 \cdot q'H_2O$$

wherein k is a number of $1.1 \pm 0.2$, p is a number of $4 \pm 1.5$ and q' is a number smaller than 1.0.

Ion Exchange Treatment

As the divalent metal, metals of group II of the Periodic Table, Ca, Mg, Zn, Ba and Sr, are advantageously used from the viewpoint of the whiteness. However, other metals such as Cu, Sn, Fe, Ni and Cr can also be used. At the ion exchange treatment, an aqueous solution of a water-soluble salt of a metal as mentioned above, for example, a chloride, a nitrate or a sulfate, is used and the solution of the metal salt is contacted with the P-type zeolite.

For the ion exchange treatment, there can be adopted a method in which the aqueous solution of the metal salt and the P-type zeolite are stirred in the state of an aqueous slurry, or a method in which the P-type zeolite is contacted with the aqueous solution of the metal salt in a fixed bed or fluidized bed. This contact can be conducted in one stage or a plurality of stages and in a continuous manner or batchwise.

It is indispensable that the ion exchange should be conducted so that at least 10 mole %, especially at least 30 mole %, of the $N_2O$ component of the P-type zeolite is replaced by MO (M represents a divalent metal). For this purpose, it is preferred that in the metal salt solution in the treatment system, the amount used of the metal salt be at least 0.5 mole, especially at least 1.0 mole, per mole of $Na_2O$ in the P-type zeolite, and the initial concentration of the aqueous solution of the metal salt be 10 to 40% by weight, especially 20 to 50% by weight. It also is preferred that the contact temperature be 20° to 100° C., especially 30° to 70° C. Of course, at a higher temperature, the exchange treatment time can be shortened. The contact time depends on the temperature or the exchange ratio, but in general, the contact time is preferably 0.5 to 3 hours.

After the ion exchange treatment, the ion-exchanged zeolite is subjected to solid-liquid separation, washed with water, dried or disintegrated according to need and then subjected to the firing treatment described below.

Firing Treatment

The ion-exchanged zeolite is fired. The firing is carried out under such conditions that the ion-exchanged zeolite is substantially rendered amorphous. The firing temperature depends on the exchange ratio and the kind of the metal salt, but the firing temperature is generally 200° to 700° C. and preferably 300° to 500° C. In general, as the metal used is heavier, the zeolite can be rendered amorphous at a relatively low temperature.

The firing can be carried out in a fixed bed, a moving bed or a fluidized bed, and it is sufficient if the treatment is 0.5 to 5 hours.

The fired product is disintegrated or pulverized, and if necessary, the classification is conducted to obtain a product of the present invention.

Amorphous Silica-Alumina Spherical articles

Each particle of the amorphous silica-alumina spherical particles of the present invention has a definite spherical form close to the true sphere and a satin-like notched surface. Preferably, the primary particle size (the particle size determined by the electron microscope method) is 0.2 to 30 $\mu m$, especially 0.3 to 10 $\mu m$. Namely, in each particle, the circularity (A) defined by the following formula:

$$A = \frac{\sqrt{r1 \cdot r2}}{r1} \quad (1)$$

wherein r1 represents the radius of the circumscribed circle of the contour of the electron microscope photo of the particle, and r2 represents the radius of the contour of the electron microscope photo of the particle, is 0.90 to 1.0, especially 0.95 to 1.0, and the notching degree (B) represented by the following formula:

$$B = \frac{\Delta t}{r1} \times 100 \quad (2)$$

wherein $\Delta t$ represents the depth between the peak and the trough in the radial direction of the indentation in the contour of the electron microscope photo of the particle.
is 1 to 10%, especially 1.5 to 5%.

The circularity (A) is an index showing the degree of the sphericity, and the notching degree is an index showing the degree of the satin-like notching of the surface of the particle.

The fact that the circularity (A) is within the above-mentioned range means that the respective particles have a form very close to the true sphere, and by dint of this feature, the particles show a good flowability and a high bulk density as the powder, and the particles exert an excellent flowability and a high bulk density to a resin and the like and an excellent dispersibility in a resin and the like.

If the notching degree (B) is within the above-mentioned range, in the case where the particles having such a satin-like notched surface are incorporated into a resin and the resin is formed into a drawn film, since the particles are mutually engaged with one another through the notched surfaces, formation of fish eyes is controlled, and when the drawn film is subjected to a surface treatment, the effect becomes especially prominent, and formation of voids is controlled and a film having an excellent transparency is obtained. Furthermore, as described hereinafter, the refractive index of the particles of the present invention is very close to those of various resins in which the particles are incorporated, and therefore, the transparency of the resins is not degraded by the incorporation of these particles. Still further, the particles of the present invention have an excellent capacity for supporting agricultural chemicals and other chemicals.

If the notching degree (B) is too low and below the above-mentioned range, the compatibility with resins tends to decrease, and if the notching degree (B) exceeds the above-mentioned range, the strength of the particles per se is reduced and the abrasion of an apparatus or the like falling in contact with the particles tends to increase.

In the present invention, if the primary particle size of the amorphous silica-alumina particles exceeds 30 $\mu m$, the particles become unsuitable for the use as a filler for resins. If the primary particle size is smaller than 0.2 $\mu m$, secondary agglomeration is caused and no good results can be obtained.

In the present invention, no loss of the alumina component is caused during the preparation as pointed out hereinbefore, and therefore, the $SiO_2/Al_2O_3$ molar ratio of the particles of the present invention is almost equal to that of the starting P-type zeolite and is in the range of from 2.5 to 4.5, especially from 3 to 4.5. In order to realize the amorphous structure and increase the refractive index, it is indispensable that the divalent metal exchange ratio $\mu m/(m+n)]$ should be at least 20%, especially at least 40%.

The refractive index of the amorphous silica-alumina particles of the present invention is generally in the range of 1.48 to 1.63 and especially in the range of 1.49 to 1.53, and this refractive index is close to those of various resins such as a methacrylic resin, polyvinyl alcohol (PVA), nylon, linear low-density polyethylene (LLDPE), low-density polyethylene, high-density polyethylene (HDPE), polypropylene (PP), an ethylene/vinyl acetate copolymer (EVA) and a vinyl chloride resin (PVC), as shown in Table A.

TABLE A

| Organic Resin Compound | Refractive Index n (—) |
|---|---|
| polyamide (nylon) | 1.53 |
| methacrylic resin | 1.49 |
| PVA | 1.50 |
| LLDPE | 1.51 |
| LDPE | 1.51 |
| HDPE | 1.54 |
| PP | 1.49 |
| EVA | 1.498 |
| PVC | 1.53 |

Furthermore, the BET specific surface area of the amorphous silica-alumina particles of the present invention is as small as less than 50 $m^2/g$, and the surface activity is low and the particles are hardly influenced in an atmosphere. The spherical particles ion-exchanged with a divalent metal are excellent in the whiteness and the whiteness by the Hunter reflection method is at least 95%.

The amorphous silica-alumina particles of the present invention can be coated or surface-treated with an inorganic oxide such as titanium oxide, silicon oxide, zirconium oxide, zinc oxide, barium oxide, magnesium oxide or calcium oxide, a silane, titanium or zirconium coupling agent, or a fatty acid, a resin acid or a derivative thereof such as a soap, an amide or an ester.

Uses

The amorphous silica-alumina particles of the present invention can be incorporated into various resins, for example, olefins resins such as polypropylene, polyethylene a crystalline propylene/ethylene copolymer, an ion-crosslinked olefin copolymer and an ethylene/vinyl acetate copolymer, thermoplastic polyesters such as polyethylene terephthalate and polybutylene terephthalate, polyamides such as 6-nylon and 6,6-nylon, chlorine-containing resins such as a vinyl chloride resin and a vinylidene chloride resin, polycarbonates, polysulfones and thermoplastic resins such as a polyacetal resin, and can be used for imparting slip and anti-blocking characteristics to formed resin molded particles such as biaxially drawn films. In case of polyamides and polyesters, the amorphous silica-alumina particles can be added before the polymerization.

Furthermore, the amorphous silica-alumina particles of the present invention can be used as a filler or reinforcer for a molding thermosetting resin or a coating-forming paint, and as a ceramic substrate.

Moreover, the amorphous spherical particles of the present invention can be used as an internal filler or coating filler for various papers.

Still further, the amorphous spherical particles can be used as a base material for cosmetics such as powder foundations, liquid (paste) foundations, baby powders and creams, as an abrasive material or a dental powder base, and as a supporting carrier for medicines, agricultural chemicals, perfumes and aromatic agents. Still in addition, the amorphous spherical particles can be used as a carrier for various chromatographies or a painting additive.

The present invention will now be described in detail with reference to the following examples that by no means limit the scope of the invention.

EXAMPLE 1

Calcium type amorphous silica-alumina particles according to the present invention were prepared by using the starting P-type zeolite synthesized according to the process described below. The obtained results are shown in Table 1.

Synthesis of Starting P-Type Zeolite

By using commercially water glass No. 3 (sodium silicate, $SiO_2=27\%$ by weight, $Na_2O=9.0\%$ by weight), sodium aluminate ($A=22.5\%$ by weight, $Na_2O=15.5\%$ by weight) and caustic soda, a dilute sodium silicate solution and a dilute sodium aluminate solution were prepared at the following molar ratios so that the total amount was 19 kg:

$Na_2O/SiO_2=0.8$,
$SiO_2/Al_2O_3=8.0$, and
$H_2O/Na_2O=70$.

In a stainless steel vessel having an inner capacity of about 25 l, 8.2 kg of the dilute sodium silicate solution was slowly mixed with 7.8 kg of the dilute sodium aluminate solution with stirring to form an alkali metal aluminosilicate homogeneous as a whole. Then, the temperature was elevated to 90° C. while violently stirring the alkali metal aluminosilicate, and the gel was maintained at this temperature for 48 hours to effect crystallization.

Then, filtration and water washing were carried out to obtain about 1.8 kg of a P-type zeolite cake having a solid concentration of 39%. Water was added to the cake so that the solid concentration was 20%, and the solids were sufficiently dispersed. Classification was carried out several times by using a small-size liquid cyclone to obtain a starting slurry to be used in the present invention.

Figure 2:
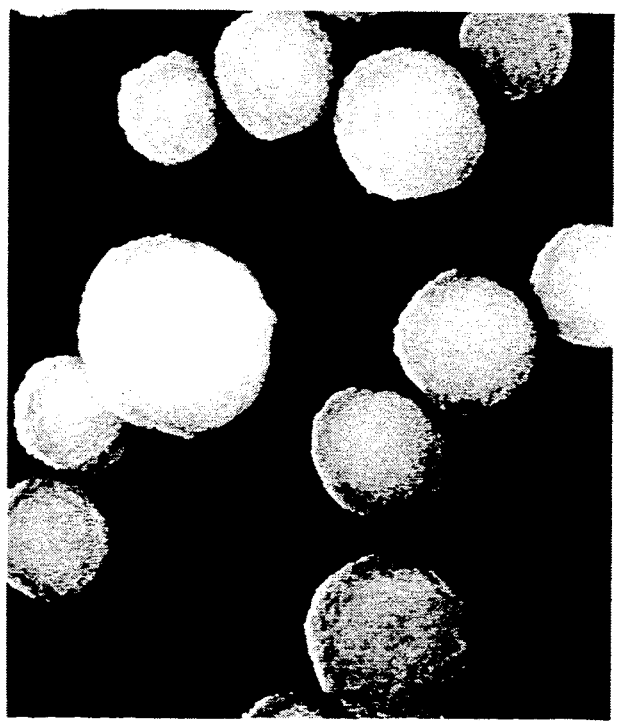
FIG. 2 is an electron microscope photo (10,000 magnifications) of particles (sample 1-0) of P-type zeolite particles used as the starting material.
Figure 3:
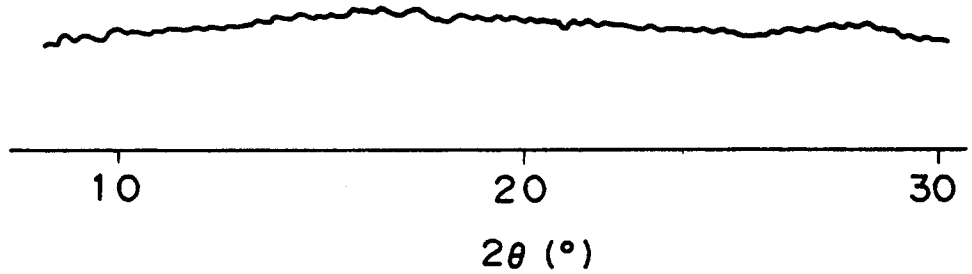
FIG. 3 is an X-ray diffraction pattern (Cu-α) of the amorphous silica-alumina spherical particles shown in FIG. 1.
Figure 4:
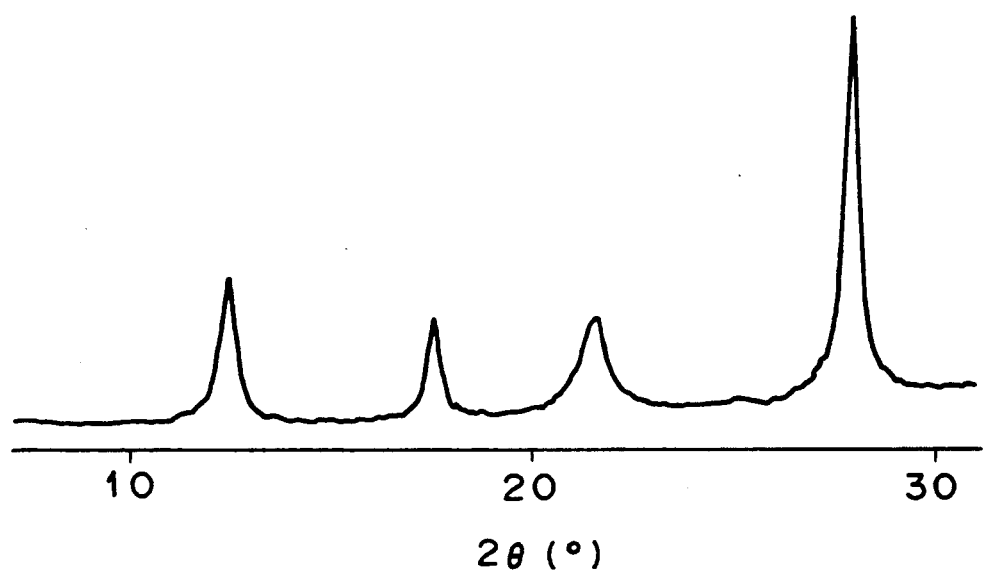
FIG. 4 is an X-ray diffraction pattern (Cu-α) of the P-type zeolite particles shown in FIG. 2.

The election microscope photo of a product (sample 1-0) obtained by drying this starting material is shown in FIG. 2, and the X-ray diffraction pattern of this dry product is shown in FIG. 4.

Calcium Type Amorphous Silica-Alumina Particles

A beaker having a capacity of 1 was charged with 500 g of the above-mentioned starting slurry, and the temperature was elevated to 40° C. in a water bath. Then, calcium choride (extra pure reagent supplied by Wako Junyaku) was added to the slurry in an amount of 0.5, 1.0 or 2.0 moles per mole of the $Na_2O$ component contained in the P-type zeolite, and the mixture was stirred for 1 hour. The mother liquid was separated by vacuum filtration. The residue was washed with water and dried at 80° C. for 24 hours, and the solid was pulverized by a sample mill and fired at a temperature of 300° to 400° C. in a small-size electric furnace. Thus, sample 1-1 through 1-7 were prepared.

With respect to the respective samples, characteristics were determined according to the following methods.

(1) Bulk Density

The bulk density was determined according to JIS K-6220-6-8.

(2) Specific Surface Area

The specific surface area was measured by the BET method using Sorptonatic Series 1800 supplied by Carlo-Erba.

(3) Whiteness

The whiteness was measured according to JIS P-8123.

(4) pH Value

The pH value of a 5% suspension was measured according to JIS K-5101-24A.

(5) Particle Size Determined Electron Microscope

An appropriate amount of a sample fine powder was placed on a metal sample plate, sufficiently dispersed and coated with a metal by a metal coating apparatus (Ion Sputter Model E-101 supplied by Hitachi) to form a sample to be projected. Then, according to customary procedures, several electron microscope photos differing in the field of vision were obtained by using a scanning electron microscope (Model S-570 supplied by Hitachi). Typical particles were selected from spherical particulate images in the fields of vision, and the diameters of the spherical particulate images were measured as the primary particle size by using a scale.

(6) Chemical Composition

The ignition loss (Ig-loss), silicon dioxide ($SiO_2$), aluminum oxide ($Al_2O_3$) and sodium oxide ($Na_2O$) were analyzed and measured according to JIS M-8852. Incidentally, the amounts of Ca, Mg, Zn and the like were determined by the atomic spectrophotoscopy.

(7) Moisture Absorption

About 1 g of the sample was charged in a weighing bottle of 40 mm × 40 mm, the weight of which had been measured in advance, and the sample was dried for 3 hours in an electric thermostat drier maintained at 150° C. and naturally cooled in a desiccator. The weight of the sample was precisely measured, and the sample was placed in a desiccator in which the relative humidity was adjusted to 90% by sulfuric acid. After 48 hours, the increase of the weight was measured as the moisture absorption.

(8) Average Particle Size

In a beaker having a capacity of 200 ml, 1 g of the sample was placed, and 150 ml of deionized was added and the sample was dispersed for 2 minutes with stirring by ultrasonic waves. The dispersion was subjected to the measurement by a 50-$\mu$m aperture tube in a Coulter counter (model TAII). The average particle size was determined from the cumulative distribution curve.

(9) X-Ray Diddractometry

The X-ray diffractometry was carried out by using an X-ray diffratometric apparatus comprising goniometer PMG-G2 and rate meter ECP-D2.

(10) Refractive Index

A solvent ($\alpha$-bromonaphthalene/kerosine), the refractive index of which had been known by the measurement using Abbe refractometer, was prepared. According to the Larsen oil immersion method described below, and several milligrams of the sample powder was placed on a slide glass, one drop of the solvent having the known refractive index was added to the powder sample. A cover glass was applied and the powder sample was sufficiently impregnated with the solvent. Then, the refractive index was determined by observing the shift of the Backe line by an optical microscope.

Larsen Oil Immersion Method

When a powder is immersed in a liquid and transmitted light is observed an optical microscope, the boundary between the powder and the liquid is seen glittering. This glittering boundary is called "Becke line". If the cylinder of the microscope is vertically moved, this Becke line shifts. Namely, when the cylinder is brought down, the bright line shifts to the inner side of the particle, and the particle is seen bright. When the cylinder is lifted up, the bright line shift outward, and the particle is seen dark. In this case, the refractive index of the liquid is judged to be larger than that of the powder. If the refractive index of the powder is larger than that of the liquid, the reverse phenomenon is observed. Accordingly, if the measurement is carried out by using appropriate liquids and two liquids having refractive indexes larger and smaller than that of the powder are selected, the intermediate value of the refractive indexes of the two liquids is designated as the refractive index of the powder.

TABLE 1

| Sample No. | 1-0 | 1-1 | 1-2 | 1-3 | 1-4 | 1-5 | 1-6 |
|---|---|---|---|---|---|---|---|
| Exchange metal | | Ca | Ca | Ca | Ca | Ca | Ca |
| Exchange quantity (molar ratio) | 0 | 0.5 | 1.0 | 2.0 | 0.5 | 1.0 | 2.0 |
| Firing temperature (°C.) | 80 | 300 | 300 | 300 | 400 | 400 | 400 |
| Bulk specific gravity (g/ml) | 0.64 | 0.75 | 0.74 | 0.73 | 0.76 | 0.76 | 0.77 |
| Specific surface area ($m^2/g$) | — | 47 | 29 | 27 | — | 24 | — |
| Whiteness (Hunter whiteness) (%) | 95 | 96 | 96 | 96 | 95 | 96 | 95 |
| pH (25° C.) | 11.2 | 8.50 | 8.61 | 8.73 | 8.7 | 8.6 | 8.7 |
| Particle size by electron microscope ($\mu$m) | 2~3 | 2~3 | 2~3 | 2~3 | 2~3 | 2~3 | 2~3 |
| Average particle size ($D_{50}$) ($\mu$m) | 3.10 | 2.89 | 2.85 | 2.82 | 2.86 | 2.75 | 2.73 |
| Moisture absorption (%) | 23.1 | 5.4 | 3.4 | 3.3 | 3.9 | 3.4 | 3.2 |
| Refractive index | 1.478 | 1.493 | 1.499 | 1.502 | 1.499 | 1.502 | 1.510 |
| Crystal form | P-type zeolite | substantially amorphous | amorphous | amorphous | amorphous | amorphous | amorphous |
| Chemical composition (wt %) (based on product dried at 110° C.) | | | | | | | |
| Ig-loss | 9.14 | 3.75 | 3.95 | 3.14 | 3.24 | 2.98 | 3.11 |
| $SiO_2$ | 51.71 | 54.74 | 54.56 | 54.95 | — | — | — |
| $Al_2O_3$ | 24.65 | 26.13 | 25.91 | 26.02 | — | — | — |
| $Na_2O$ | 14.50 | 10.18 | 8.48 | 8.11 | — | — | — |
| exchange metal | — | 4.89 | 6.74 | 7.26 | — | — | — |

EXAMPLE 2

Amorphous silica-alumina particles of the barium, zinc, magnesium and strontium types according to the present invention were prepared by using sample 1-0 in the same manner as described in Example 1. The obtained results are shown in Table 2.

TABLE 2

| Sample No. | 1-0 | 2-1 | 2-2 | 2-3 | 2-4 |
|---|---|---|---|---|---|
| Exchange metal | | Ba | Zn | Mg | Sr |
| Exchange quantity (molar ratio) | 0 | 1.0 | 1.0 | 1.0 | 1.0 |
| Firing temperature (°C.) | 80 | 400 | 400 | 400 | 400 |
| Bulk specific gravity (g/ml) | 0.64 | 0.76 | 0.73 | 0.68 | 0.77 |
| Specific surface area ($m^2/g$) | — | 17 | 38 | 43 | 31 |
| Whiteness (Hunter whiteness) (%) | 95 | 97 | 97 | 96 | 96 |
| pH (25° C.) | 11.2 | 8.10 | 8.23 | 9.79 | 8.70 |
| Particle size by electron microscope ($\mu$m) | 2~3 | 2~3 | 2~3 | 2~3 | 2~3 |
| Average particle size ($D_{50}$) ($\mu$m) | 3.10 | 2.90 | 2.88 | 3.14 | 3.06 |
| Moisture absorption (%) | 23.1 | 2.7 | 3.0 | 8.5 | 3.2 |
| Refractive index | 1.478 | 1.518 | 1.497 | 1.485 | 1.502 |
| Crystal form | P-type zeolite | amorphous | amorphous | substantially amorphous | amorphous |
| Chemical composition (wt %) (based on product dried at 110° C.) | | | | | |
| Ig-loss | 9.14 | 2.97 | 2.88 | 3.54 | 3.72 |
| $SiO_2$ | 51.71 | 52.73 | 53.63 | 54.63 | 50.57 |
| $Al_2O_3$ | 24.65 | 25.63 | 25.30 | 26.18 | 24.27 |
| $Na_2O$ | 14.50 | 4.64 | 8.69 | 12.90 | 7.09 |

TABLE 2-continued

| Sample No. | 1-0 | 2-1 | 2-2 | 2-3 | 2-4 |
|---|---|---|---|---|---|
| exchange metal | — | 13.47 | 9.24 | 2.48 | 13.96 |

EXAMPLE 3

Amorphous silica-alumina particles of the calcium, barium and zinc types were prepared in the same manner as described in Example 1 except that the composition of the starting P-type zeolite was changed as follows (sample 3-0). The obtained results are shown in Table 3.

Composition (molar ratio) of P-Type Zeolite:

$Na_2O/SiO_2 = 0.7$
$SiO_2/Al_2O_3 = 8.0$
$H_2O/Na_2O = 90$

TABLE 3

| Sample No. | 3-0 | 3-1 | 3-2 | 3-3 |
|---|---|---|---|---|
| Exchange metal | — | Ca | Ba | Zn |
| Exchange quantity (molar ratio) | — | 1.0 | 1.0 | 1.0 |
| Firing temperature (°C.) | (80) | 400 | 400 | 400 |
| Bulk specific gravity (g/ml) | 0.79 | 0.94 | 0.97 | 0.92 |
| Specific surface area (m²/g) | — | 20 | 19 | 32 |
| Whiteness (Hunter whiteness) (%) | 95.4 | 96.3 | 97.1 | 96.8 |
| pH (25° C.) | 11.0 | 8.4 | 7.9 | 8.2 |
| Particle size by electron microscope (μm) | 5~7 | 5~7 | 5~7 | 5~7 |
| Average particle size (D$_{50}$) (μm) | 6.8 | 6.5 | 6.3 | 6.6 |
| Moisture absorption (%) | 1.2 | 3.4 | 3.1 | 3.8 |
| Refractive index | 1.478 | 1.502 | 1.521 | 1.500 |
| Crystal form | P-type zeolite | amorphous | amorphous | amorphous |
| Chemical composition (wt %) (based on product dried at 110° C.) | | | | |
| Ig-loss | 9.06 | 3.25 | 2.84 | 3.01 |
| SiO$_2$ | 53.10 | 55.46 | 53.67 | 54.33 |
| Al$_2$O$_3$ | 23.87 | 25.78 | 25.13 | 24.86 |
| Na$_2$O | 14.01 | 8.80 | 4.93 | 8.73 |
| exchange metal | — | 6.52 | 13.09 | 8.99 |

EXAMPLE 4

Amorphous silica-alumina particles of the calcium, barium and zinc types were prepared in the same manner as described in Example 1 except that a P-type zeolite having a composition described below, which was prepared by using, as the silicic acid component, an active silicic acid gel of fine particles obtained by acid-treating active clay produced as Nakajo, Niigata Prefecture, Japan, a clay of the smectite group, was used as the starting P-type zeolite. The obtained results are shown in Table 4.

Composition (molar ratio) of Starting P-Type Zeolite:

$Na_2O/SiO_2 = 0.55$
$SiO_2/Al_2O_3 = 6.0$
$H_2O/Na_2O = 65$

TABLE 4

| Sample No. | 4-0 | 4-1 | 4-2 | 4-3 |
|---|---|---|---|---|
| Exchange metal | — | Ca | Ba | Zn |
| Exchange quantity (molar ratio) | — | 1.0 | 1.0 | 1.0 |
| Firing temperature (°C.) | (80) | 400 | 400 | 400 |
| Bulk specific gravity (g/ml) | 0.51 | 0.62 | 0.68 | 0.67 |
| Specific surface area (m²/g) | — | 44 | 26 | 39 |
| Whiteness (Hunter whiteness) (%) | 95.4 | 96.2 | 97.3 | 97.1 |
| pH (25° C.) | 11.2 | 8.6 | 8.1 | 8.3 |
| Particle size by electron microscope (μm) | 1~2 | 1~2 | 1~2 | 1~2 |
| Average particle size (D$_{50}$) (μm) | 2.10 | 1.81 | 1.80 | 1.94 |
| Moisture absorption (%) | 22.7 | 3.4 | 2.7 | 3.1 |
| Refractive index | 1.483 | 1.497 | 1.512 | 1.497 |
| Crystal form | P-type zeolite | amorphous | amorphous | amorphous |
| Chemical composition (wt %) (based on product dried at 110° C.) | | | | |
| Ig-loss | 8.51 | 2.78 | 3.02 | 3.40 |
| SiO$_2$ | 52.36 | 55.21 | 53.06 | 54.30 |
| Al$_2$O$_3$ | 24.38 | 26.57 | 25.33 | 25.06 |
| Na$_2$O | 14.59 | 8.22 | 4.70 | 8.04 |
| exchange metal | — | 7.02 | 13.88 | 10.12 |

EXAMPLE 5

A beaker having a capacity of 2 l was charged with 200 g of the calcium type amorphous silica-alumina particles of sample 1-2 prepared in Example 1 and 1 l of water, and the mixture was heated at 60° C. with stirring.

Then, 200 g of a titanium sulfate having a concentration of 5% by weight as TiO$_2$ and a 10% by weight aqueous solution of NaOH were simultaneously added to the formed slurry over a period of 2 hours while maintaining the pH value at 8.5.

Then, the mixture was stirred and aged in this state for 1 hour, and the mother liquid was separated by suction filtration and the residual solid was sufficiently washed with water and dried at 110° C.

The obtained dry powder was pulverized by a sample mill and fired at 800° C. for 2 hours by an electric furnace to obtain titanium oxide-covered calcium type amorphous silica-alumina spherical particles (sample 5-1). The obtained sample was tested in the same manner as described in Example 1. The obtained results are shown in Table 5.

EXAMPLE 6

A beaker having a capacity of 1 l was charged with 200 g of the barium amorphous silica-alumina particles of sample 2-1 prepared in Example 2 and 400 ml of water, and the mixture was stirred to obtain a homogeneous slurry. Barium hydroxide was added to the slurry in an amount of 10% by weight as BaO based on the solid in the slurry. The mixture was stirred at 80° C. for 1 hour.

neous slurry was formed in the same manner as described in Example 6.

Then, 30 g of commercially available finely divided silica, white carbon (Mizukasil® P-527 supplied by Mizusawa Industrial Chemicals, Ltd), was gradually added to the slurry, and the mixture was stirred for 30 minutes.

Then, 96 g of lime milk was gradually added to the slurry with stirring so that the dispersion concentration was 7.9 g/100 ml as CaO, and the dispersion was treated at 90° C. for 2 hours.

Then, the mother liquid was separated by suction filtration, and the cake was directly dried in an oven at 110° C., pulverized by a sample mill and fired at 300° C. for 2 hours to obtain calcium silicate-covered calcium type amorphous silica-alumina spherical particles (sample 7-1). The obtained results are shown in Table 5.

TABLE 5

| Sample No. | 5-1 | 6-1 | 7-1 |
| --- | --- | --- | --- |
| Exchange metal | Ca | Ba | Ca |
| Exchange quantity (molar ratio) | — | — | — |
| Firing temperature (°C.) | 800 | 800 | 300 |
| Bulk specific gravity (g/ml) | 0.72 | 0.80 | 0.36 |
| Specific surface area ($m^2/g$) | — | — | 48 |
| Whiteness (Hunter whiteness) (%) | 97 | 97 | 98 |
| pH (25° C.) | 8.6 | 7.7 | 9.8 |
| Particle size by electron microscope ($\mu m$) | 2~3 | 2~3 | 2~3 |
| Average particle size ($D_{50}$) ($\mu m$) | 2.89 | 3.62 | 3.08 |
| Moisture absorption (%) | — | — | 8.8 |
| Refractive index | 1.625 | 1.624 | 1.481 |
| Crystal form | amorphous | amorphous | slight peak of Ca—Si |
| Chemical composition (wt %) (based on product dried at 110° C.) | | | |
| Ig-loss | 1.21 | 1.04 | 3.31 |
| $SiO_2$ | 54.90 | 50.16 | 58.01 |
| $Al_2O_3$ | 26.09 | 24.36 | 22.23 |
| $Na_2O$ | 7.12 | 3.21 | 7.20 |
| exchange metal | 6.03 | 21.23 | 9.06 |

Then, the mixture was directly dried in a drier at 110° C. The dry solid was pulverized by a sample mill and fired at 800° C. for 2 hours to obtain barium oxide-coated silica-alumina spherical particles (sample 6-1). The obtained results are shown in Table 5.

EXAMPLE 7

A beaker having a capacity of 2 l was charged with 200 g of the calcium type particles of sample 1-2 prepared in Example 1 and 800 ml of water, and a homogeneous slurry

COMPARATIVE EXAMPLE

Commercially available A-type zeolite, X-type zeolite and Y-type zeolite were calcium-exchanged and fired in the same manner as described in Example 1 to obtain samples H-1 through H-6. The obtained results are shown in Table 6.

TABLE 6

| Sample No. | H-1 | H-2 | H-3 | H-4 | H-5 | H-6 |
| --- | --- | --- | --- | --- | --- | --- |
| Zeolite | A-type | A-type | A-type | X-type | Y-type | X-type |
| Exchange metal | — | Ca | Ca | Ca | Ca | Zn |
| Exchange quantity (molar ratio) | 0 | 1.0 | 1.0 | 1.0 | 1.0 | 2.0 |
| Firing temperature (°C.) | 80 | 300 | 500 | 500 | 500 | 500 |
| Bulk specific gravity (g/ml) | | 0.51 | 0.46 | 0.45 | 0.41 | 0.47 |
| Specific surface area ($m^2/g$) | | 630 | 603 | 710 | 704 | 716 |
| Whiteness (Hunter whiteness) (%) | 96.2 | 96.5 | 96.1 | 94.8 | 95.4 | 96.1 |
| pH (25° C.) | | 9.8 | 10.1 | 9.7 | 9.6 | 9.9 |
| Particle size by electron microscope ($\mu m$) | 1~2 | 1~2 | 1~2 | 2~4 | 2~4 | 2~4 |
| Average particle size ($D_{50}$) ($\mu m$) | 2.0 | 2.0 | 2.0 | 3.15 | 2.50 | 3.20 |
| Moisture absorption (%) | 27.8 | 24.6 | 23.4 | 29.5 | 27.0 | 29.4 |
| Refractive index | 1.47 | 1.471 | 1.478 | 1.479 | 1.472 | 1.484 |
| Crystal form | A-type zeolite | A-type zeolite | A-type zeolite | X-type zeolite | Y-type zeolite | X-type zeolite |
| Chemical composition (wt %) (based on product dried at 110° C.) | | | | | | |
| Ig-loss | — | 3.60 | — | 2.46 | 3.05 | 3.00 |
| $SiO_2$ | — | 40.66 | — | 49.42 | 56.50 | 44.26 |
| $Al_2O_3$ | — | 36.38 | — | 32.49 | 25.86 | 29.51 |
| $Na_2O$ | — | 4.78 | — | 8.49 | 7.91 | 8.07 |
| exchange metal | — | 14.09 | — | 6.68 | 6.70 | 15.14 |

EXAMPLE 8

An additive shown in Table 7 was added to low density polyethylene having a melt flow rate of 1.5 g/10 min and a density of 0.920 g, and the mixture was melt-kneaded at 150° C. by an extruder and was then pelletized.

The pellet was fed to an extruder and a film having a thickness of 50 μm was prepared by the inflation film-forming method at a melting zone temperature of 160° C. and a die temperature of 170° C.

The following physical properties of the obtained film were measured. The obtained results are shown in Table 7.

Haze

The haze was determined according to ASTM D-1003.

Blocking Resistance

Two films were piled and a load of 200 g/cm² was applied, and the piled films were allowed to stand still at 40° C. for 24 hours. The blocking resistance was evaluated based on whether or not the piled films could be easily peeled from each other, according to the following scale:

⊚: the films were peeled without any resistance
○: the films were peeled only with slight resistance
Δ: the films were peeled relatively difficultly
X: peeling was very difficult

Gloss

⊚: very good gloss
○: good gloss
Δ: relatively bad gloss
X: bad gloss

TABLE 7

| Run No. | Additive | Amount Incorporated (%) | Haze (%) | Blocking Resistance | Initial Coloration |
|---|---|---|---|---|---|
| 1 | sample 1-5 | 0.30 | 6.9 | ⊚ | not observed |
| 2 | sample 1-5*1 | 0.30 | 6.9 | ⊚ | not observed |
| 3 | sample 2-2 | 0.30 | 6.5 | ⊚ | not observed |
| 4 | diatomaceous earth | 0.30 | 11.2 | Δ | not observed |
| 5 | synthetic silica*2 | 0.30 | 7.6 | Δ | not observed |
| 6 | not added | 0 | 6.3 | X | not observed |

Note
*1sample coated with Mitsui Hi-Wax 110P in amount of 10% based on sample
*2Siloid #244

EXAMPLE 9

An additive shown in Table 8 was added to polypropylene, and the obtained composition was extrusion-molded by a T-die to obtain an undrawn film.

The undrawn film was drawn at a draw ratio of 6 in the longitudinal direction and at a draw ratio of 6 in the lateral direction, and the film having a thickness of 30 μm was evaluated according to the methods described in Example 8.

In Table 8, the number of fish eyes having a size of at least 0.1 mm per 500 cm² of the film is shown as the fish eye.

TABLE 8

| Run No. | Additive | Amount Incorporated*1 (ppm) | Haze (%) | Blocking Resistance | Initial Coloration | Fish Eye (number) |
|---|---|---|---|---|---|---|
| 1 | sample 4-1 | 1500 | 2.8 | ⊚ | not observed | 15 |
| 2 | sample 4-1*2 | 1500 | 2.6 | ⊚ | " | 17 |
| 3 | sample 4-1*3 | 1500 | 1.9 | ⊚ | " | 19 |
| 4 | sample 4-1*4 | 1500 | 2.0 | ⊚ | " | 8 |
| 5 | sample 4-1*5 | 1500 | 1.4 | ⊚ | " | 10 |
| 6 | sample 4-1*6 | 1500 | 1.6 | ⊚ | " | 20 |
| 7 | synthetic silica*7 | 1500 | 2.9 | ○ | " | 63 |
| 8 | not added | — | 0.5 | X | " | — |

Note
*1amount (net) of powdery particles
*2sample 4-1 coated with 3% of silane coupling agent (A-1100 supplied by Nippon Unicar)
*3sample 4-1 coated with 20% of PP wax (Viscol 660P supplied by Sanyo Kasei)
*4product obtained by adding 50 parts of terpene resin (Clearon P-105 supplied by Yasuhara Yushi) to particles of sample 4-1, melt-mixing them and pulverizing mixture to particles having size of about 1 mm
*5product obtained by adding 50 parts of erucic amide (Arflow P-10 supplied by Nippon Yushi) to particles of sample 4-1, melt-dispersing the mixture, cooling the melt and forming the solid to particles having size of about 1 mm
*6sample 4-2 surface-treated with PE emulsion (Permaline PN supplied by Sanyo Kasei) having PE concentration of 10%
*7Siloid #150

EXAMPLE 10

By using the titanium-coated silica-alumina spherical particles (sample 5-1) obtained in Example 5, a powder foundation was prepared.

| Component (A) | |
|---|---|
| Mica | 34 parts |
| Talc | 10 parts |
| Titanium dioxide | 20 parts |
| Coloring pigment | 5 parts |
| Titanium-coated spherical silica-alumina particles | 15 parts |
| Component (B) | |
| Squalene | 5.0 parts |
| Lanolin | 4.0 parts |
| Isopropyl myristate | 3.0 parts |
| Surface active agent | 1.0 part |
| Perfume | appropriate amount |

Predetermined amounts of the silica, talk, titanium dioxide, coloring pigment and spherical silica-alumina particles of component (A) were weighed, and they were charged in a stainless steel vessel and sufficiently mixed. The mixture was pulverized by an atomizer and blended by a Henschel mixer. Then, a heated mixture of component (B) was added to and sufficiently mixed with the above mixture to obtain a product.

The obtained foundation and a foundation free of spherical silica-alumina particles were subjected to a comparative test by randomly selected 20 persons having an age of 20 to 50. It was generally judged that the foundation containing the spherical silica-alumina particles had a good spread and gave a smooth and refreshed finish. Moreover, it was judged that the foundation containing the spherical silica-alumina particles had a good air permeability.

EXAMPLE 11

A transparent toothpaste having a relatively soft grinding power, containing as the grinding cleaning agent the amorphous silica-alumina spherical particles (sample 1-2) having a notched surface, which was obtained in Example 1, and having a composition described below was prepared.

| Component | Amount (% by weight) |
| --- | --- |
| Particles (sample 1-2) | 20 |
| Sorbitol syrup | 60 |
| Polyethylene glycol #400 | 5 |
| Sodium lauryl sulfate | 2.3 |
| Carboxymethyl cellulose | 2.5 |
| Perfume | 1.2 |
| Water | 9 |

The obtained semi-transparent paste had a cleaning power desirable for a toothpaste.

EXAMPLE 12

A copy paper having a base weight of 5 g/m² was coated with the following composition containing silica-alumina spherical particles. The physical properties of the coated paper were determined, and the obtained results are shown in Table 10.

| Coating Composition | |
| --- | --- |
| 0.5% Solution of sodium pyrophosphate | 20 g |
| 10.0% starch solution (MS #4600 supplied by Nippon Shokuhin Kako) | 3 g |
| 50% SBR (Dow 620) | 3.4 g |
| Silica-alumina spherical particles | 18 g |
| Deionized water | 5.4 g |

The coating operation was carried out by using coating rod No. 10.

The opacity was evaluated according to the following scale.

◯: when paper was piled on bar cord, the bar cord was hardly seen through paper

Δ: when paper was piled on bar cord, the bar cord was fairly seen through paper

X: when paper was piled on bar cord, the bar cord was clearly seen through paper

TABLE 9

| Run No. | Additive | Amount Coated (g/m²) | Whiteness (%) | Opacity | Touch |
| --- | --- | --- | --- | --- | --- |
| 1 | sample 1-6 | 12.2 | 84.3 | ◯ | good |
| 2 | sample 2-6 | 11.8 | 84.1 | ◯ | good |
| 3 | sample 2-2 | 12.0 | 83.8 | ◯ | good |
| 4 | sample 5-1 | 12.2 | 85.2 | ◯ | good |
| 5 | sample 6-1 | 12.3 | 84.8 | ◯ | good |
| 6 | calcium carbonate | 12.1 | 82.7 | Δ | slightly bad |
| 7 | blank | — | 82.3 | X | slightly bad |

We claim:

1. Amorphous silica-alumina spherical particles having a chemical composition represented by the following general formula:

$$mMO \cdot nNa_2O \cdot pSiO_2 \cdot Al_2O_3 \cdot qH_2O$$

wherein M represents at least one member selected from the group consisting of divalent metals, $m+n$ is a number of $1.1\pm0.2$, the m/n ratio is in the range of from 10/0 to 1/9, p is a number of $4\pm1.5$ and q is a number smaller than 0.5, each particle having a definite spherical form as a whole and a notched surface, wherein the moisture absorption determined after standing at a relative humidity of 90% and room temperature for 48 hours is lower than 13% and the refractive index is 1.48 to 1.61.

2. Amorphous silica-alumina spherical particles as set forth in claim 1, which have a BET specific surface area smaller than 50 m²/g.

3. Amorphous silica-alumina spherical particles as set forth in claim 1, which have a primary particle size of 0.2 to 30 μm as determined by the electron microscope method.

4. Amorphous silica-alumina spherical particles as set forth in claim 1, which have a whiteness of at least 95% as determined by the Hunter reflection method.

5. Amorphous silica-alumina spherical particles as set forth in claim 1, wherein the spherical particles are surface-treated with at least one member selected from the group consisting of inorganic oxides, silane, titanium and zirconium coupling agents, and fatty acids and resin acids and derivatives thereof.

6. A filler for an organic polymer, which comprises silica-alumina spherical particles as set forth in either one of claim 1 or claim 5.

7. Amorphous silica-alumina spherical particles as set forth in claim 1, wherein said divalent metals are selected from the group consisting of Ca, Mg, Zn, Ba and Sr.

* * * * *